United States Patent
Willis et al.

(10) Patent No.: US 8,718,773 B2
(45) Date of Patent: May 6, 2014

(54) OPTIMIZING ENERGY TRANSMISSION IN A LEADLESS TISSUE STIMULATION SYSTEM

(75) Inventors: N. Parker Willis, Atherton, CA (US);
Axel F. Brisken, Fremont, CA (US);
Mark W. Cowan, Fremont, CA (US);
Michael Pare, San Francisco, CA (US);
Robert Fowler, Danville, CA (US);
James Brennan, Santa Clara, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 934 days.

(21) Appl. No.: 11/752,775

(22) Filed: May 23, 2007

(65) Prior Publication Data

US 2008/0294208 A1 Nov. 27, 2008

(51) Int. Cl.
*A61N 1/18* (2006.01)
*A61N 1/378* (2006.01)

(52) U.S. Cl.
CPC .................................. *A61N 1/3787* (2013.01)
USPC .................. 607/33; 607/34; 607/61

(58) Field of Classification Search
USPC .......... 607/3–4, 9, 17–18, 38, 30, 32–33, 37, 607/60–62; 600/437, 439, 442, 444, 600/447–450, 463, 472; 128/903
See application file for complete search history.

(56) References Cited

U.S. PATENT DOCUMENTS

| | | | |
|---|---|---|---|
| 3,659,615 A | 5/1972 | Enger | |
| 3,693,627 A | 9/1972 | Berkovits | |
| 3,698,398 A | 10/1972 | Berkovits | |
| 3,735,756 A | 5/1973 | Richards et al. | |
| 3,832,994 A | 9/1974 | Bicher et al. | |
| 3,857,382 A | 12/1974 | Williams et al. | |
| 3,939,844 A | 2/1976 | Peuignot | |
| 3,942,534 A | 3/1976 | Allen et al. | |
| 4,181,133 A | 1/1980 | Kolenik et al. | |
| 4,256,115 A | 3/1981 | Bilitch | |
| 4,265,228 A | 5/1981 | Zoll | |
| 4,280,502 A | 7/1981 | Baker, Jr. et al. | |

(Continued)

FOREIGN PATENT DOCUMENTS

| | | |
|---|---|---|
| DE | 4330680 | 3/2005 |
| WO | WO 99/61058 | 12/1999 |
| WO | WO 03/070323 | 8/2003 |
| WO | WO 2007/149936 A2 | 12/2007 |

OTHER PUBLICATIONS

Abraham et al., for the Miracle study group, "Cardiac Resynchronization in Chronic Heart Failure," N Engl J Med, 2002;346:1845-53.

(Continued)

*Primary Examiner* — Kennedy Schaetzle
*Assistant Examiner* — Erica Lee
(74) *Attorney, Agent, or Firm* — Wilson Sonsini Goodrich & Rosati

(57) ABSTRACT

Method and systems for optimizing acoustic energy transmission in implantable devices are disclosed. Transducer elements transmit acoustic locator signals towards a receiver assembly, and the receiver responds with a location signal. The location signal can reveal information related to the location of the receiver and the efficiency of the transmitted acoustic beam received by the receiver. This information enables the transmitter to target the receiver and optimize the acoustic energy transfer between the transmitter and the receiver. The energy can be used for therapeutic purposes, for example, stimulating tissue or for diagnostic purposes.

32 Claims, 7 Drawing Sheets

(56) References Cited

U.S. PATENT DOCUMENTS

| | | |
|---|---|---|
| 4,561,442 A | 12/1985 | Vollmann et al. |
| 4,577,633 A | 3/1986 | Berkovits et al. |
| 4,651,716 A | 3/1987 | Forester et al. |
| 4,690,144 A | 9/1987 | Rise et al. |
| 4,830,006 A | 5/1989 | Haluska et al. |
| 5,018,523 A | 5/1991 | Bach, Jr. et al. |
| 5,063,928 A | 11/1991 | Grevis |
| 5,103,129 A | 4/1992 | Slayton et al. |
| 5,113,859 A | 5/1992 | Funke |
| 5,165,403 A | 11/1992 | Mehra |
| 5,170,784 A | 12/1992 | Ramon |
| 5,174,289 A | 12/1992 | Cohen |
| 5,193,539 A | 3/1993 | Schulman et al. |
| 5,292,338 A | 3/1994 | Bardy |
| 5,377,166 A | 12/1994 | Kuhn |
| 5,405,367 A | 4/1995 | Schulman et al. |
| 5,411,535 A | 5/1995 | Fujii et al. |
| 5,433,731 A | 7/1995 | Hoegnelid et al. |
| 5,674,251 A | 10/1997 | Combs et al. |
| 5,749,909 A | 5/1998 | Schroeppel et al. |
| 5,751,539 A | 5/1998 | Stevenson et al. |
| 5,757,104 A | 5/1998 | Getman |
| 5,766,227 A | 6/1998 | Nappholz et al. |
| 5,800,464 A | 9/1998 | Kieval |
| 5,814,089 A | 9/1998 | Stokes et al. |
| 5,817,130 A | 10/1998 | Cox et al. |
| 5,844,349 A * | 12/1998 | Oakley et al. ............ 310/358 |
| 5,871,506 A | 2/1999 | Mower |
| 5,935,158 A | 8/1999 | Holmstrom et al. |
| 5,978,204 A | 11/1999 | Stevenson |
| 5,998,910 A | 12/1999 | Park et al. |
| 6,037,704 A | 3/2000 | Welle |
| 6,070,101 A | 5/2000 | Struble et al. |
| 6,078,837 A | 6/2000 | Peterson et al. |
| 6,110,098 A | 8/2000 | Renirie et al. |
| 6,141,588 A * | 10/2000 | Cox et al. .................... 607/9 |
| 6,208,894 B1 * | 3/2001 | Schulman et al. .......... 607/2 |
| 6,223,079 B1 | 4/2001 | Bakels et al. |
| 6,233,484 B1 | 5/2001 | Ben-Haim et al. |
| 6,330,475 B1 | 12/2001 | Renirie et al. |
| 6,366,816 B1 | 4/2002 | Marchesi |
| 6,408,205 B1 | 6/2002 | Renirie et al. |
| 6,424,234 B1 | 7/2002 | Stevenson |
| 6,439,236 B1 | 8/2002 | Porter et al. |
| 6,445,953 B1 | 9/2002 | Bulkes et al. |
| 6,534,895 B2 | 3/2003 | Kadota et al. |
| RE38,119 E | 5/2003 | Mower |
| 6,628,989 B1 | 9/2003 | Penner et al. |
| 6,645,145 B1 | 11/2003 | Dreschel et al. |
| 6,647,292 B1 | 11/2003 | Bardy et al. |
| 6,654,638 B1 | 11/2003 | Sweeny |
| 6,671,547 B2 | 12/2003 | Lyster et al. |
| 6,707,230 B2 | 3/2004 | Smith et al. |
| 6,721,597 B1 | 4/2004 | Bardy et al. |
| 6,754,528 B2 | 6/2004 | Bardy et al. |
| 6,754,531 B1 | 6/2004 | Kroll et al. |
| 6,764,446 B2 | 7/2004 | Wolinsky et al. |
| 6,788,974 B2 | 9/2004 | Bardy et al. |
| 6,798,716 B1 | 9/2004 | Charych |
| 6,834,204 B2 | 12/2004 | Osteroff et al. |
| 6,856,835 B2 | 2/2005 | Bardy et al. |
| 6,983,185 B2 | 1/2006 | Ley et al. |
| 7,010,350 B2 | 3/2006 | Kralik |
| 7,024,248 B2 | 4/2006 | Penner et al. |
| 7,198,603 B2 | 4/2007 | Penner et al. |
| 7,200,437 B1 | 4/2007 | Nabutovsky et al. |
| 7,283,874 B2 | 10/2007 | Penner |
| 7,610,092 B2 | 10/2009 | Cowan et al. |
| 2004/0015104 A1 | 1/2004 | Goldberger |
| 2004/0172083 A1* | 9/2004 | Penner ...................... 607/35 |
| 2004/0243192 A1* | 12/2004 | Hepp et al. ................ 607/17 |
| 2004/0260214 A1 | 12/2004 | Echt et al. |
| 2006/0136004 A1 | 6/2006 | Cowan et al. |
| 2006/0136005 A1 | 6/2006 | Brisken et al. |
| 2007/0055184 A1 | 3/2007 | Echt et al. |
| 2007/0078490 A1 | 4/2007 | Cowan et al. |
| 2007/0293912 A1 | 12/2007 | Cowan et al. |

OTHER PUBLICATIONS

ACC/AHA Task Force on Practice Guidelines, "Evaluation and Management of Chronic Heart Failure in the Adult," JACC 2002;38:2101-13.

Allessie et al., "Regional Control of Atrial Fibrillation by Rapid Pacing in Conscious Dogs," Circulation 1991;84:1689-97.

Ansalone et al., "Bi-ventricular Pacing I Heart Failure:Back to Basics in the Pathophysiology of Left Bundle Branch Block to Reduce the Number of Nonresponders," Am J Cardiol 2003;91:55F-61F.

Auricchio et al., "Cardiac Resynchronization Therapy: Current State of the Art," Circulation 2004;109:300-307.

Bardy et al., "The Totally Subcutaneous ICD System (The S-ICD)," PACE. 2002; 24,578.

Becker et al, "Suppression of Atrial Fibrillation by Multisite and Septal Pacing in a Novel Experimental Model", Cardiovascular Research 2001;54(2):476-481.

Bradley et al., "Cardiac Resynchronization and Death from Progressive Heart Failure: A Meta-Analysis of Randomized Controlled Trials," JAMA 2003;289:730-740.

Camm et al., Chapter 6: Nonpharmaceutical treatment of atrial fibrillation, In Atrial Fibrillation. Facts from Yesterday—Ideas for tomorrow. Futura Publishing Company, Inc., Armonk, NY, 1994, pp. 125-147.

Dalecki et al., "Effects of Pulsed Ultrasound on the Frog Heart: I. Thresholds for Changes in Cardiac Rhythm and Aortic Pressure," Ultrasound in Med. & Biol. 1993; 19:385-390.

Dalecki et al., "Effects of Pulsed Ultrasound on the Frog Heart: II. An Investigation of Heating as a Potential Mechanism," Ultrasound in Med. & Biol. 1993; 19:391-398.

Dalecki et al., "Thresholds for premature ventricular contractions in frog hearts exposed to lithotripter fields," Ultrasound in Med. & Biol. 1991; 17:341-346.

Daoud et al., "Implantation Techniques and Chronic Lead Parameters of Biventricular Pacing Dual-chamber Defibrillators," J Cardiovasc Electrophysiology 2002; 13:964-970.

Daubert et al., "Permanent Left Ventricular Pacing With Transvenous Leads Inserted Into The Coronary Veins," PACE 1998;21;239-245.

Daubert et al., "Use of Specifically Designed Coronary Sinus Leads for Permanent Left Ventricular Pacing: Preliminary Experience," PACE, 1997; 20: II-NASPE Abstract 17, Apr. 1997.

David Trial Investigators, "The Dual Chamber and VVI Implantable Defibrillator (DAVID) Trial," JAMA 2002;288:3115-3123.

Deshmukh et al. "Direct His-bundle pacing: present and future," PACE 2004;27 [Pt.II]:862-70.

Ellenbogen et al., "Detection and Management of An Implantable Cardioverter Defibrillator Lead Failure," JACC. 2003;41:73-80.

Feldman et al, "Comparison of medical therapy, resynchronization and defibrillation therapies in heart failure trial (COMPANION)," Presented at ACC 2003 Late Breaking Clinical Trials, 1 page.

Franz, "Mechano-electrical feedback in ventricular myocardium," Cardiovascular Research. 1996; 32:15-24.

Gregoratos et al., ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation. 2002; 106:2145-2161.

Hu et al., "Stretch-Activated Ion Channels in the Heart," J. Mol. Cell Cardiol. 1997; 29:1511-1523.

Johnson et al., "Adaptive Pacing During Ventricular Fibrillation," PACE 2003;26:1824-36.

Kalman J.M. et al, "Regional Entrainment of Atrial Fibrillation in Man", J Cardiovasc Electrophysiol 1991;7:867-76.

Kass et al., "Improved Left Ventricular Mechanics from Acute VDD Pacing in Patients with Dilated Cardiomyopathy and Ventricular Conduction Delay," Circulation 1999;99:1567-73.

(56) References Cited

OTHER PUBLICATIONS

Kenknight B.H. et al, "Regional Capture of Fibrillating Ventricular Myocardium" Circ Res 1999;77:849-55.retrieve from the Internet: <<http://circres.ahajournals.org/cgi/content/full/77/4/849>>.

Kohl et al., Stretch-Induced Changes in Heart Rate and Rhythm: Clinical Observations, Experiments and Mathematical Models. Progress in Biophysics & Molecular Biology, 1999; 71:91-138.

Kohl et al., "Sudden Cardiac Death by Commotio Cordis: Role of Mechano-Electrical Feedback," Cardiovascular Research, 2001; 50:280-289.

Leclercq et al, "Is Dual Site Better than Single Site Atrial Pacing in the Prevention of Atrial Fibrillation?" PACE 2000;23:2102-7.

Leclercq et al., "Systolic Improvement and Mechanical Resynchronization does not Require Electrical Synchrony in the Dilated Failing Heart with Left Bundle-Branch Block", Circulation 2002;106:1760-1763.

Leclerq et. al., "Acute Hemodynamic Effects of Biventricular DDD Pacing in Patients with End-Stage Heart Failure", JACC 1998;32:1825-1831.

Lee et al., "Effect of implantable Defibrillators of Arrhythmic Events and Mortality in the Multicenter Unsustained Tachycardia Trial," Circulation. 2002; 106:233-238.

Linde et al., "Long-Term Benefits of Biventricular Pacing in Congestive Heart Failure: From the Multisite Stimulation in Cardiomyopathy (MUSTIC) Study", J Am Coll Cardiol 2002;40:111-118.

Miracle Trial Investigators, "Combined Cardiac Resynchronization and Implantable Cardioversion Defibrillation in Advanced Heart Failure: the Miracle ICD Trial," JAMA 2003;289:2685-2694.

Mirza et al, "Biatrial Pacing for Paroxysmal Atrial Fibrillation", J Am Coll Cardiol 2002;40:457-463.

Moss et al., "Prophylactic Implantation of a Defibrillator in Patients with Myocardial Infarction and Reduced Ejection Fraction," N Engl J Med. 2002; 346:877-933.

Niehaus et al., "Non-Contact Cardiac Stimulation with locused Ultrasound Pulses," PACE 2003: 26:1023.

Nielsen et al., "A Randomized Comparison of Atrial and Dual-Chambered Pacing in 177 Consecutive Patients With Sick Sinus Syndrome," J Am Coll Cardiol 2003;42:614-623.

Nolte et al., "Mechanically Induced Ventricular Extrasystoles in the Isolated Perfused Guinea-Pig Heart," Arzneim.-Forsch/Drug Research. 1987; 37(11): 1025-1029.

Peschar et al., "Left Ventricular Septal and Apex Pacing for Optimal Pump Function in Canine Hearts," J Am Coll Cardiol, 2003;41:1218-26.

Reiter et al.., "Effects of Mechano-Electrical Feedback: Potential Arrhythmogenic Influence in Patients With Congestive Heart Failure," Cardiovascular Research, 1996; 32:44-51.

Smailys et al., "Investigation of the Possibilities of cardiac Defibrillation by Ultrasound," Resuscitation, 1981; 9:233-242.

Sowton, "Clinical Results with the Tachylog Antitachycardia Pacemaker", PACE 1984; 7(Part II):1313-1317.

Tacker, Chapter 1: Fibrillation causes and criteria for defibrillation. In Defibrillation of the Heart. Tacker, WA, ed. Mosby-Year Book, Inc., St. Louis, Missouri, 1994, pp. 1-14.

The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," N Engl J Med.,1997;337: 1576-1583.

Valls-Bertault et al., "Adverse Events with Transvenous Left Ventricular Pacing in Patients with Severe Heart Failure: Early Experience from a Single Centre," Europace, 2001;3:60-63.

Warren et al., "Clinical Evaluation of Automatic Tachycardia Diagnosis by an Implanted Device", PACE 1986;9 (Part II):1079-1083.

International Search Report and Written Opinion of PCT Application No. PCT/US08/63669, dated Jul. 17, 2008, 12 pages total.

Extended Search Report of European Patent Application No. 08755507.4, filed Jun. 7, 2010, 7 pages total.

\* cited by examiner

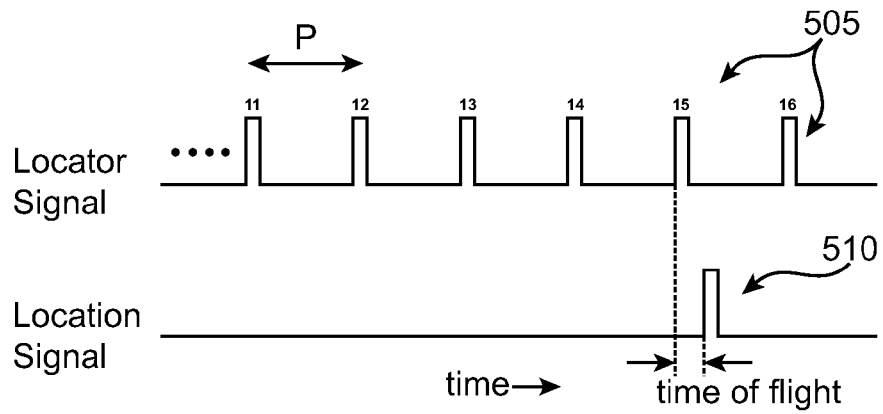
FIG. 6A
FIG. 6B
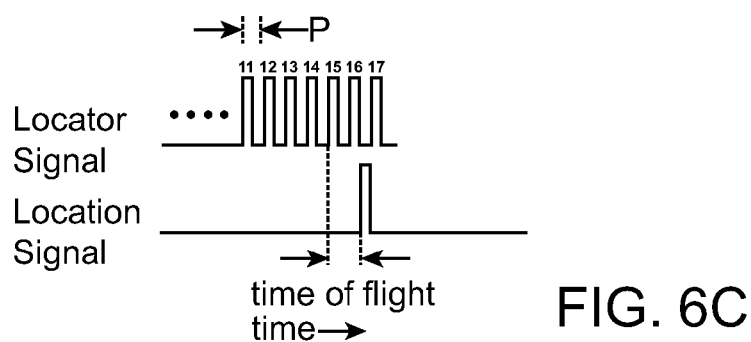
FIG. 6C
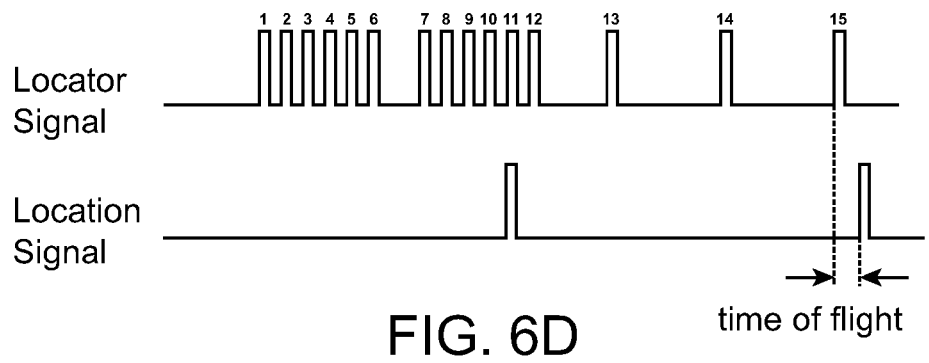
FIG. 6D

OPTIMIZING ENERGY TRANSMISSION IN A LEADLESS TISSUE STIMULATION SYSTEM

CROSS-REFERENCES TO RELATED APPLICATIONS

The subject matter of this application is related to that of the following commonly owned patent applications: Ser. No. 11/315,524, Ser. No. 11/535,857, Ser. No. 11/315,023. The full disclosures of each of these prior filings are incorporated herein by reference but the benefit of the filing dates is not being claimed.

FIELD OF THE INVENTION

This invention generally relates to optimizing acoustic or ultrasound energy transmission and energy conversion and more particularly to optimizing acoustic energy transmission and conversion in implantable devices.

BACKGROUND OF THE INVENTION

Stimulation of cardiac tissue using a leadless cardiac stimulation system has been disclosed earlier by the applicant. Generally, such a system comprises an arrangement of one or more acoustic transducers, and associated circuitry, referred to as a controller-transmitter, and one or more implanted receiver-stimulator devices. The controller-transmitter generates and transmits acoustic energy, which is received by the receiver-stimulator, and the receiver-stimulator in turn converts the acoustic energy into electrical energy, which is delivered to the tissue through electrodes.

The controller-transmitter may be externally coupled to the patient's skin, but will usually be implanted, requiring that the controller-transmitter have a reasonable size, similar to that of implantable pacemakers, and that the controller-transmitter be capable of operating for a lengthy period, typically three or more years, using batteries. The small size and long operational period require that the system efficiently utilize the acoustic energy from the controller-transmitter with minimal dissipation or dispersion of the transmitted energy and efficient conversion of the energy by the receiver-stimulator.

Charych (U.S. Pat. No. 6,798,716) describes various strategies for locating an acoustic receiver. Charych describes methods for charging wireless devices (receivers) from a controller-transmitter that is powered through a plug, providing power in excess of 1000 W. In contrast, a leadless cardiac stimulation system, where the power flow is 6 orders of magnitude lower, requires completely different methods and systems for locating the receiver, which are not described by Charych.

Briefly, in its simplest form, the receiver-stimulator comprises one or more acoustic piezoelectric receiver elements, one or more rectifier circuits, and electrodes. The piezoelectric receiver elements couple power from the acoustic field generated by the controller-transmitter and convert it into electric power. If applied directly to the tissue this AC electrical power does not stimulate the tissue because its frequency is too high for excitation/stimulation. In order to initiate a paced heart beat, or provide other therapeutic stimulation to tissues, the rectifier circuits convert all or some of the available AC electrical power to an electrical pulse that is applied to the cardiac tissue through the electrodes. The acoustic field is generated and transmitted either by an externally placed or an implantable controller-transmitter that is remote from the location of the receiver-stimulator.

The acoustic energy generated by the controller-transmitter is generally referred to as an acoustic beam or ultrasound beam and is characterized by acoustic intensity (I) measured in Watts/square meter. In order to create an acoustic intensity of Io over an area Ao the controller-transmitter must expend at least Io*Ao Watts of power. Only the portion of this acoustic beam that intersects the receiver-stimulator will be available as electrical power. If the area Ao is larger than the cross sectional area or aperture of the receiver Ar, then the ratio Ar/Ao represents that fraction of the power in the acoustic beam that is available to the receiver-stimulator. Therefore the optimally efficient acoustic beam is very narrow and only intersects the receiver elements of the receiver-stimulator.

The controller-transmitter has one or more piezoelectric transducers that convert electrical power into acoustic power creating the acoustic beam that is directed at the receiver-stimulator. The ability of the controller-transmitter to generate this acoustic beam over a small area is characterized by its focal or directivity gain. In general the larger the cross sectional area (referred to as the aperture) of the controller-transmitter transducers, the higher the directivity gain will be. This requires the controller-transmitter to have a wide aperture transmitter that focuses acoustic energy at the receiver-stimulator. It also requires the controller-transmitter to steer or direct the acoustic beam at the receiver-stimulator. This can be accomplished by using a phased array that uses beam-forming techniques to steer the acoustic beam at the receiver-stimulator. Steering can be accomplished by adjusting the phases and amplitudes of the electrical drive signals to the transducer array, which results in adjusting the direction and focal distance of the transmitted beam.

If the location of the receiver-stimulator or the controller-transmitter does not change over time, the controller-transmitter could be configured at the time of implant to optimally select a focused beam profile that is aimed at the receiver-stimulator location determined at the implantation time. However, in the case of the leadless system, the receiver-stimulator can be expected to move due to cardiac motion, breathing, or body orientation. Moreover, the controller-transmitter may move slightly due to body orientation or body movements or migration. Therefore, to accommodate the movement of the controller-transmitter and the receiver-stimulator, inventors herein have realized that successful operation in the simplest implementation would require a relatively broad beam acoustic emission. However, in this mode of operation most of the transmitted acoustic energy may pass by the receiver-stimulator and not used efficiently. Hence, inventors herein have further realized that to improve efficiency the transmit beam needs to be significantly sharpened or focused, and reliable operation would require continuous, specific knowledge of the location of the receiver-stimulator.

For the above reasons, it would be desirable to provide a leadless system that efficiently transmits and receives acoustic energy. It would also be desirable for the transmitted beam to be adjusted, to be as focused as possible at targeting the receiving element(s) of the receiver-stimulator. It would be particularly desirable if the location of the receiver-stimulator is known to the controller-transmitter, and, thereby, a focused acoustic beam could be aimed and transmitted toward the receiver-stimulator. It would also be desirable if the receiver-stimulator is located using mechanisms that minimize the size and complexity of the receiver-stimulator such that additional circuitry or energy consumption is not imposed upon the receiver-stimulator.

BRIEF SUMMARY OF THE INVENTION

Systems and methods are provided for efficiently delivering acoustic energy from an implanted or externally applied acoustic transmitter to an implanted acoustic receiver. The acoustic energy is converted by the receiver into electrical energy which can be used for a variety of purposes. The electrical energy will typically be delivered to electrodes in contact with tissue in order to stimulate tissue, for example, in cardiac pacing for bradycardia, for termination of tachyarrhythmia, for bi-ventricular resynchronization therapy for heart failure, or the like. The systems and methods of the present invention could also be used in a variety of other applications, including applications for nerve stimulation, brain stimulation, voluntary muscle stimulation, gastric stimulation, bone growth stimulation, pain amelioration, sensing and communication of local diagnostic information, and the like, where an acoustic transmitter has to efficiently transmit energy to an implanted receiver. The implanted acoustic receiver could act as a tissue stimulator (receiver-stimulator) or act more generally as an acoustic energy converter (receiver-converter). Efficient transmission can be achieved by deploying strategies for locating the receiver and then transmitting a focused acoustic beam specifically aimed at the receiver and thereby improving operational efficiency of the system. These systems and methods are particularly useful when the transmitter is an implantable device dependent on a limited source of energy, such as a battery.

By "locator signal" we mean an acoustic signal transmitted by the transducer element(s) of a controller-transmitter assembly to elicit a "location signal."

By "location signal" we mean a signal that is either passively or actively generated by the receiver-stimulator. The location signal may be in response to a "locator signal" transmitted by the controller-transmitter or may be periodically transmitted by the receiver-stimulator. The location signal is used by the controller-transmitter to determine the location of the receiver relative to the controller-transmitter, thus allowing the controller-transmitter to direct a focused, efficient acoustic beam at the receiver-stimulator.

One exemplary embodiment of the invention is a system for focusing acoustic energy into a human body. The system comprises an array of acoustic transducers configured to transmit acoustic energy into the body; circuitry for focusing the acoustic energy at specific regions in the body; an acoustic receiver adapted to receive the acoustic energy and convert the acoustic energy into electrical energy; a pair of electrodes connected to the acoustic receiver and adapted to transfer the electrical energy to the body; wherein the circuitry is further configured to detect the electrical energy transferred through the body by these electrodes to determine whether the acoustic energy is focused on the acoustic receiver. The circuitry could have one or more pairs of electrodes that are configured to determine whether the acoustic energy is focused on the acoustic receiver. The circuitry could also be configured for sequentially transmitting the acoustic energy.

Another exemplary embodiment of the invention described herein is a system for stimulating tissue comprising an implantable acoustic controller-transmitter comprising an array of acoustic transducers configured to transmit focused acoustic energy; one or more implantable acoustic receiver-stimulators adapted to receive the acoustic energy and convert the acoustic energy into electrical energy, wherein the receiver-stimulator further comprises electrodes configured to be in electrical communication with the tissue; and the electrical energy is delivered between the electrodes; and wherein the controller-transmitter is configured to determine the location of one or more of the receiver-stimulators relative to the controller-transmitter so that the controller-transmitter can direct the focused acoustic energy to one or more of the receiver-stimulators.

Another embodiment of this invention is a method and system for determining the location of an acoustic receiver in the body. An array of acoustic transducers is used to transmit acoustic energy at a specific location in the body. The acoustic receiver is configured with electrodes that generate an electric location signal whenever it receives acoustic energy. Separate detection electrodes can detect the electric location signal indicating when the array of acoustic transducers is focused on the acoustic receiver and revealing the location of the receiver. The transducer array could be configured to sequentially steer the acoustic energy until the location signal is detected or a preset time limit has been reached. The transmitted acoustic energy could be a focused acoustic beam. The location signal could be detected by a sensing circuit on the controller-transmitter.

In another embodiment of the invention, the controller-transmitter would be further configured to adjust the transducer array to transmit focused acoustic energy to the region of the tissue associated with detecting the location signal. This focused energy could be adequate to stimulate tissue and, in particular, cardiac tissue. In yet another embodiment, this focused energy would be generated based on characteristics of the location signal.

In yet another embodiment of this invention, an implantable acoustic controller-transmitter comprises an adjustable transducer array configured to transmit acoustic energy into tissue; an implantable acoustic receiver-converter comprises a transducer assembly adapted to receive the acoustic energy and convert the acoustic energy to electrical energy, where the transmitter is configured to transmit an acoustic locator signal towards the receiver, and the receiver is configured to generate a location signal. The location signal could be either an electrical output or an acoustic transmission in response to the locator signal. The locator signal could be focused acoustic energy. Alternatively, the focused acoustic energy that is transmitted by the transmitter can be converted to electrical energy by the receiver-converter and stored in the receiver-converter as electrical energy to be discharged at the appropriate moment. The electrical energy could also be used to operate various circuitry, such as the control circuitry, diagnostic sensing circuitry or communication circuitry.

Another exemplary embodiment of this invention is a system for stimulating tissue comprising an implantable acoustic controller-transmitter with an acoustic transducer array adapted to transmit acoustic energy into tissue; and an implantable acoustic receiver-stimulator which receives acoustic energy and converts the acoustic energy to electrical energy and which has a first electrode assembly connected to the receiver-stimulator and adapted to be in electrical communication with the tissue, wherein the receiver-stimulator periodically transmits a location signal, and wherein the controller-transmitter detects the location signal. The location signal could be an electrical output or an acoustic transmission that could be sensed by the controller-transmitter. Based on the characteristics of the location signal, the transducer array could be adjusted to transmit focused acoustic energy towards the receiver-stimulator. The characteristics of the location signal would include frequency, duration, amplitude, phase, and time of flight of the location signal. The invention is also a method for optimizing acoustic energy transmission in tissue between an implantable controller-transmitter and one or more implantable receiver-stimulators comprising transmitting an acoustic locator signal from the controller-transmitter towards the receiver-stimulator, wherein the controller-transmitter comprises an adjustable transducer array; and generating a location signal from the receiver-stimulator in response to receiving the locator signal. The method could include detecting the location signal using the controller transmitter and adjusting the transducer array. The transducer array can transmit focused acoustic energy towards the receiver-stimulator. Additionally, the method could include adjusting the transducer array sequentially to transmit focused locator signals to regions of the tissue until the receiver-stimulator location signal is detected by the controller-transmitter or a pre-set time limit has been reached; and adjusting the transducer array to transmit focused acoustic energy to the region associated with the detected location signal. The method could further include converting the acoustic energy using the receiver-stimulator, and applying the converted energy to the tissue. The energy could be of sufficient magnitude to stimulate tissue.

BRIEF DESCRIPTION OF THE DRAWINGS

FIGS. 6A-6D show methods for minimizing scan time for target detection.

DETAILED DESCRIPTION OF THE INVENTION

Figure 1:
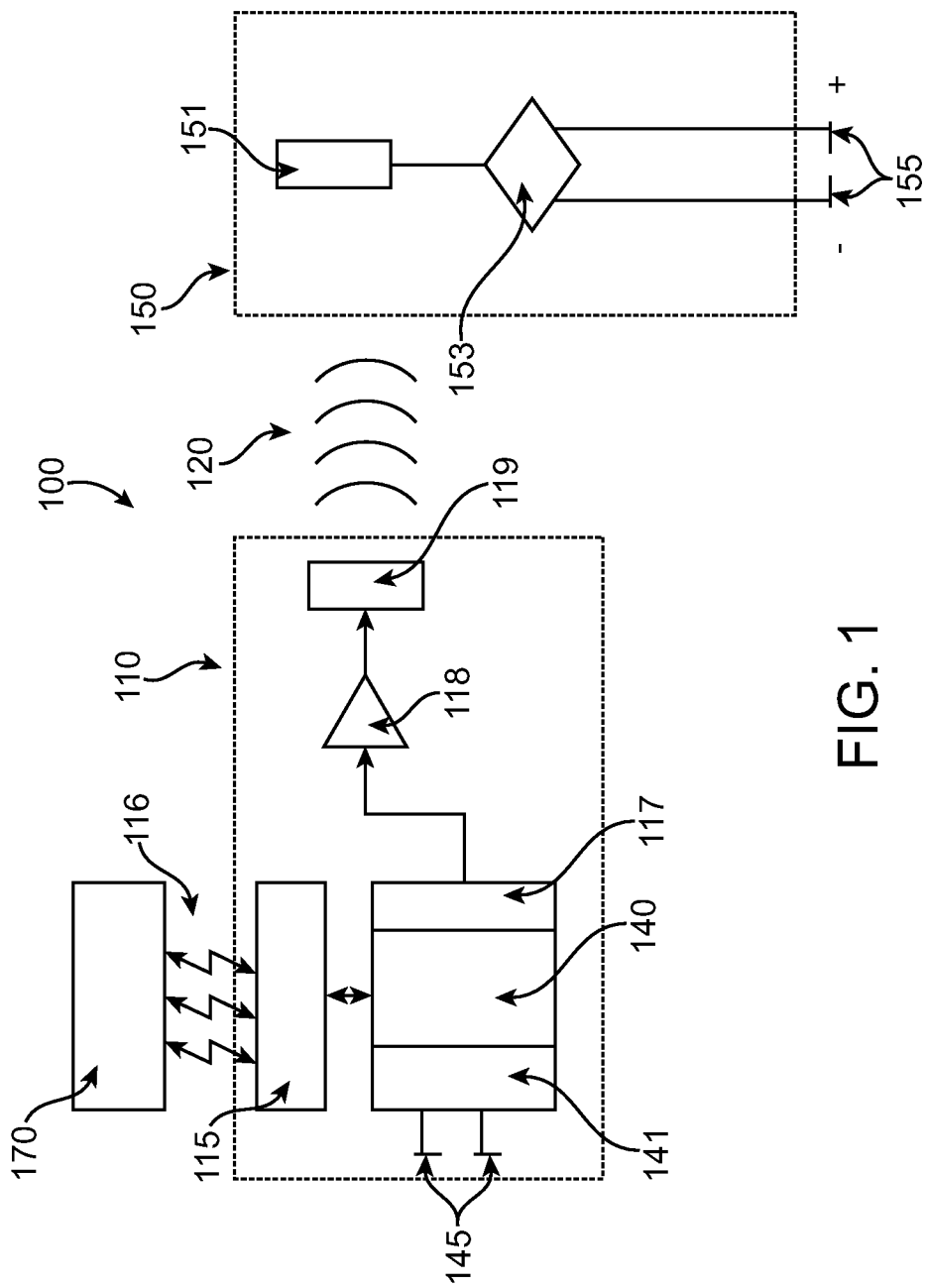
FIG. 1 is a block diagram illustrating a tissue stimulation system.

A leadless tissue stimulation system is shown in FIG. 1 as system 100. An implantable or external controller-transmitter module 110 generates acoustic waves 120 of sufficient amplitude and frequency and for a duration and period such that the receiver-stimulator module 150 electrically stimulates tissue. An external programmer 170 wirelessly communicates with an implantable controller-transmitter module 110, typically by radio frequency telemetry means 116, to adjust operating parameters. The implantable controller-transmitter module comprises a telemetry receiver 115 for adjusting the transmit acoustic characteristics, control circuitry 140 and signal generator 117, a power amplifier 118, and an output transducer assembly 119 for generating the acoustic beam 120 transmitted to receiver-stimulator 150. Understandably, the controller-transmitter 110 transfers acoustic energy to the receiver-stimulator 150 leadlessly. Control circuitry 140 contains an electrical signal sensing circuit element 141 connected to one or more sensing electrodes 145 disposed on the outer casing of the controller-transmitter or connected via cables to the controller-transmitter. Alternatively, electrical sensing circuit 141 may be a typical electrogram sensing circuit or may be an electrical spike detection circuit.

The receiver-stimulator 150 comprises a piezoelectric receiving transducer 151, rectifier circuitry 153, and tissue contacting electrodes 155. In this embodiment, acoustic energy received and rectified by the receiver-stimulator is directly applied to the electrodes 155. Alternatively, the receiver-stimulator module may comprise multiple transducer/rectifier channels in a variety of combinations, which may be in series or parallel orientations, or the construction may perform impedance matching, and/or for signal filtering as previously disclosed in co-pending application Ser. No. 11/315,524, to increase the efficiency of the receiver-stimulator.

Figure 2A:
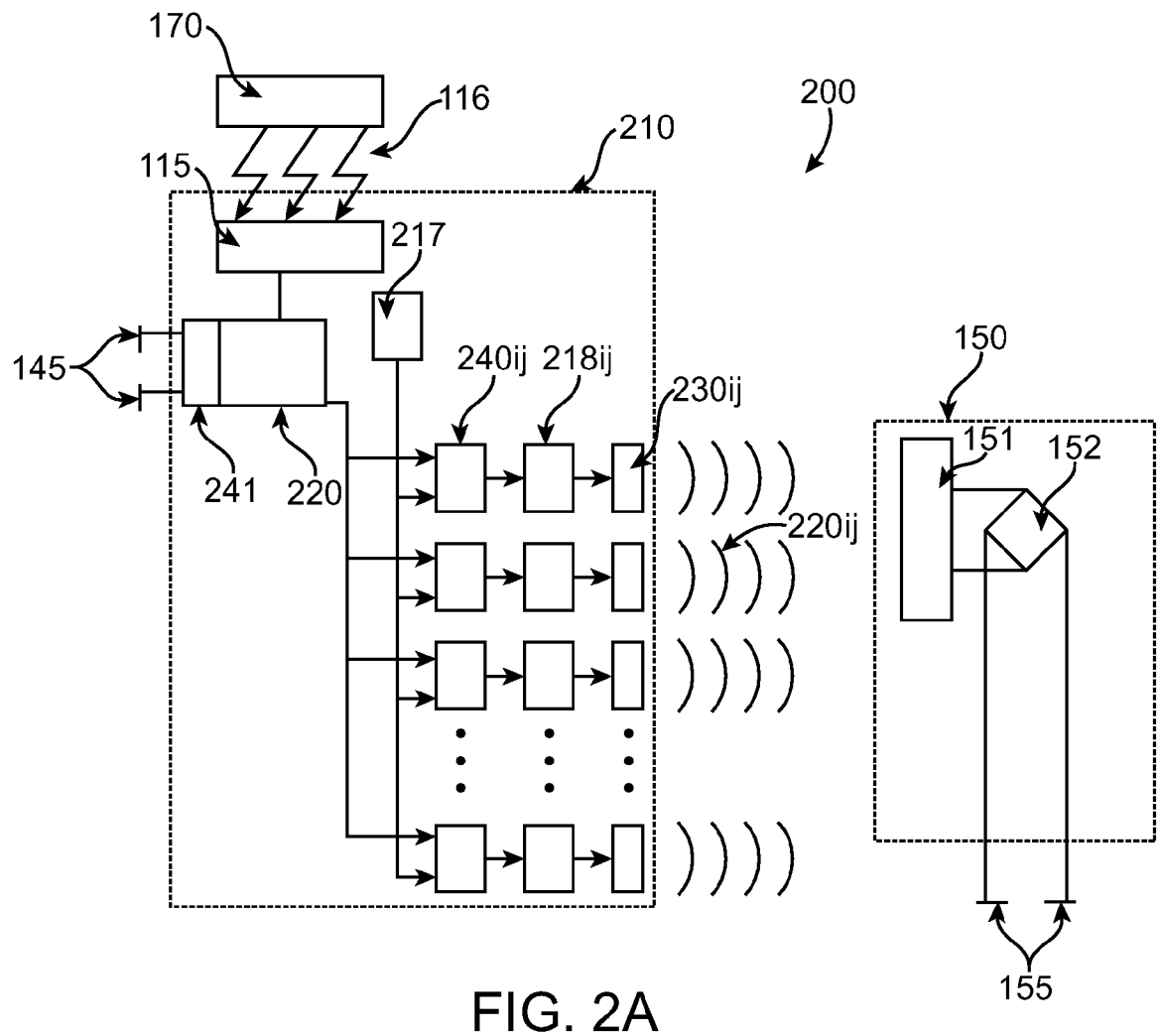
FIGS. 2A-B illustrate one embodiment of this invention.
Figure 2B:
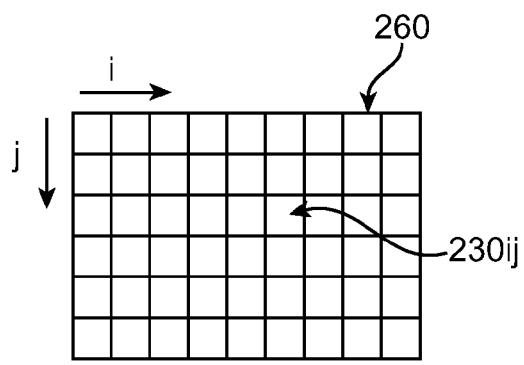

One embodiment of the present invention is shown in FIG. 2A as system 200. The controller-transmitter module 210 is placed either inside the body, but remote from myocardial tissue, or outside the body in contact with the body surface. The external programmer 170 communicates with the controller-transmitter module, typically by radio frequency telemetry 116. The telemetry module 115 inside the controller-transmitter unit 210 provides two-way communications directly with the control circuitry 220. A separate continuous wave (CW) signal generator 217 inside the controller-transmitter 210 provides the acoustic operating frequency for the system. The control circuitry 220 and signal generator 217 are both connected to each channel of a two dimensional acoustic transducer array 260 (shown in FIG. 2B), where each channel comprises a transmit/receive transducer element 230$ij$, a power amplifier 218$ij$ and phase shifter module 240$ij$. The phase shifter module 240$ij$, ensures that during acoustic transmissions, each channel transmits with the correct phase so as to form a efficient, focused narrow acoustic beam intended to precisely intercept the receiver-stimulator. A control signal from control circuitry 220 defines the transmit phases. The output of the phase shifter 240$ij$ then passes to the power amplifier 218$ij$ of the channel, which is also under the control of the control circuitry 220, and which can be either in an OFF state, a full ON state, or at selected levels of intermediate power which might be required for beam shading. The output of the power amplifier passes directly to the channel transducer element 230$ij$. One embodiment of using the phase shifter for each output channel has been described above. Other techniques can also be employed, such as direct formatting of the transmit beam by the control circuitry 220.

The controller-transmitter 210 would scan a spatial region by sending narrow acoustic beams (the locator signals), looking for a response (the location signal), from the receiver-stimulator. If the focused, directed acoustic beam intersects the receiver-transmitter the acoustic energy is converted by the receiver-stimulator and delivered as an electrical output onto the electrodes 155. This electrical output would generate an electrical signal that would be detected by sensing electrodes 145 and detection circuits 241 of the controller-transmitter 210. If the controller-transmitter does not detect an electrical signal within a reasonable time frame, the inference would be that the directed acoustic beam did not intersect the receiver-stimulator and the directed acoustic beam was "off target." Such time frames may be predetermined or determined based on location signal characteristics. Then, the controller-transmitter would adjust the focused, directed beam to another portion of the region where the receiver-stimulator may be located, possibly chosen to be close to the previous region, and repeat the locator signal transmission thereby scanning the spatial region iteratively. In this manner, an electrical signal will be generated and detected if the receiver-stimulator is in the spatial region being scanned. The controller-transmitter then uses the focused, directed beam parameters that resulted in a detected electrical signal (location signal) as the target (transmission region) for the efficient transmission of a narrow acoustic beam of acoustic energy towards the receiver-stimulator. Alternatively, the controller-transmitter could then analyze characteristics of the detected electrical signal to determine whether the directed transmitter beam was adequately targeting the receiver-stimulator.

Figure 3:
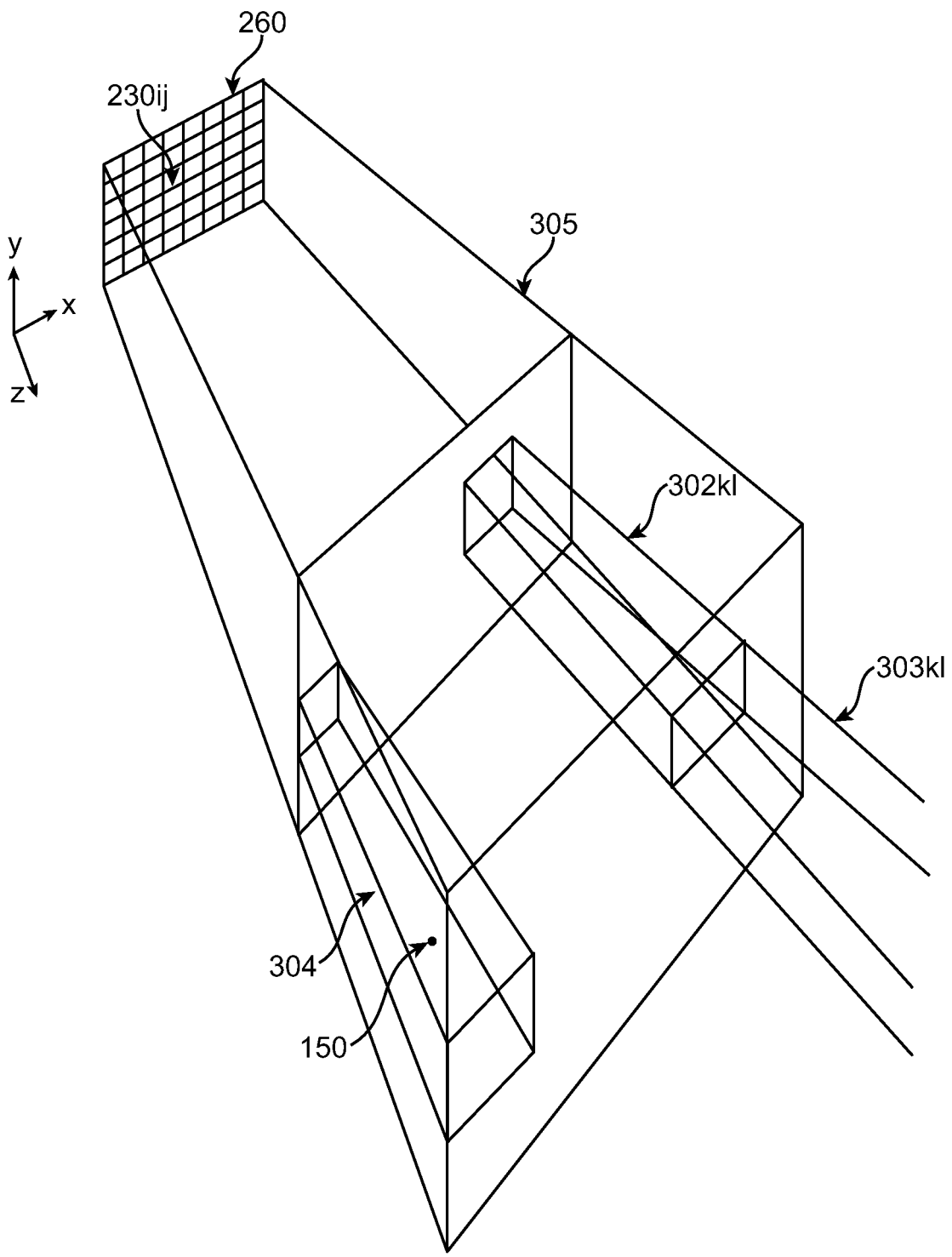
FIG. 3 illustrates the acoustic array scanning a region for location signals in response to locator signals.

The scanning process is shown in more detail in FIG. 3. The phased array 260 of the controller-transmitter is composed of individual transducers 230$ij$. For convenience the array is oriented in the x-y plane at z=0. The spatial volume to be scanned 305 encompasses all of the possible locations for the receiver-stimulator, and, again for convenience, is located in the z>0 half space with respect to the phased array 260. The extent of 305 is constrained by anatomical limits and may vary depending on the specific stimulation application. The spatial volume 305 is broken up into multiple volumes 302$kl$, which are individually scanned or tested. The volumes 302$kl$ may overlap; however, it is desirable to have the entire collection of volumes cover the region 305. The array is aimed at a volume 302$kl$ by setting the appropriate phase parameters for the array elements 230$ij$.

The following method, provided as an example, can be used for determining the correct phase parameter for each of the array elements. A spatial location v1 for the volume 302$kl$ is picked; it is typically, but not necessarily, the center of the volume. A spatial location v2 for the array element 230$ij$ is chosen; typically, but not necessarily, the center of the array element. Note in general that v1 and v2 are 3D vectors with x, y and z components. The phase is given by $$\phi = \left(2\pi \frac{\|v1 - v2\|_2}{\lambda}\right) \mod 2\pi \quad \text{(Equation 1)}$$

where $\|\;\|_2$ is the standard Euclidean norm or distance function and mod is the modulo arithmetic operator and $\lambda$ is the wavelength of the acoustic wave. Alternatively, the phase parameters may not be computed modulo $2\pi$ but rather modulo $n2\pi$ where n is the maximum phase delay, in wavelengths, across elements of the array 260 when aiming at the farthest angular extent of region 305. This is slightly more efficient and therefore preferred because the first cycle of the transmitted array will be targeted at the volume 302$kl$ whereas modulo $2\pi$ phase results in the first n cycles of the transmitted wave being out of focus.

Typically the x, y width of each volume 302$kl$ will be selected as the width of the narrowest acoustic beam that is possible from the array 260. This minimal acoustic beam width w is approximated by $$w = \frac{\lambda}{D} r$$

where $\lambda$ is the wavelength of the acoustic wave, D is the lateral size of the array 260, and r is the range or distance along the z axis from the array 260 to the volume 302$kl$. Therefore, if the array 260 is rectangular, i.e., different lateral widths in the x and y dimension, then the minimal beam width and hence x and y dimensions of the volume 302$kl$ will be different. Also note that since the minimal acoustic beam width increases with range r, the volume 302$kl$ is in general wedge shaped, expanding in lateral dimension with increased range r. The acoustic beam itself tapers off from a center peak rather than ending abruptly therefore it is desirable for the volumes 302$kl$ to have some overlap, for example 50% overlap. This provides finer targeting of the receiver-stimulator and hence more efficient transfer of acoustic energy.

The maximum lateral width, W, of the interrogation region 305 is approximated by $$W = \frac{\lambda}{d} r$$

where $\lambda$ is the wavelength of the acoustic wave, d is the lateral size of an individual array element 230$i$, and r is the range or distance along the z axis from the array 260 to the volume 302$kl$. Similar to the individual volumes 302$kl$ the entire scan region 305 has a wedge shape expanding out in lateral dimension with increasing range r.

If 305 lies entirely in the far field of the array 260 then depth or z focusing is not required and each volume 302$kl$ can be extended over the entire z depth of region 305. However, if 305 overlaps with the near field transmission region of the phased array 260, multiple layers of volumes 302$kl$, 303$kl$, etc. must be scanned in the z dimension as well. Generally speaking, the boundary between the near and far field regions is given by $$r = \frac{D^2}{4\lambda}$$

Of course, in situations where the possible target location region is either in the far field or moves only within a fixed focal zone, then scanning in the z dimension may not be required.

Another method for quickly and efficiently determining the required phasing for the elements of the transmit array in the controller-transmitter is described below. As described previously, the required phasing can be calculated; however, this is computationally expensive, which consumes valuable energy and time, particularly because it involves the calculation of a square root. One alternative is to pre-compute the required phases for each element 230$ij$ of the array 260 for each scan location 302$kl$. This, however, quickly results in a significant amount of required memory. There is the additional burden of the time required to read the phases out of memory and load them into the phase shifter 240$ij$ for each of the array elements 230$ij$. This time can be reduced by increasing the clock speed of the digital electronics in the controller-transmitter or paralleling the loading process.

Figure 4:
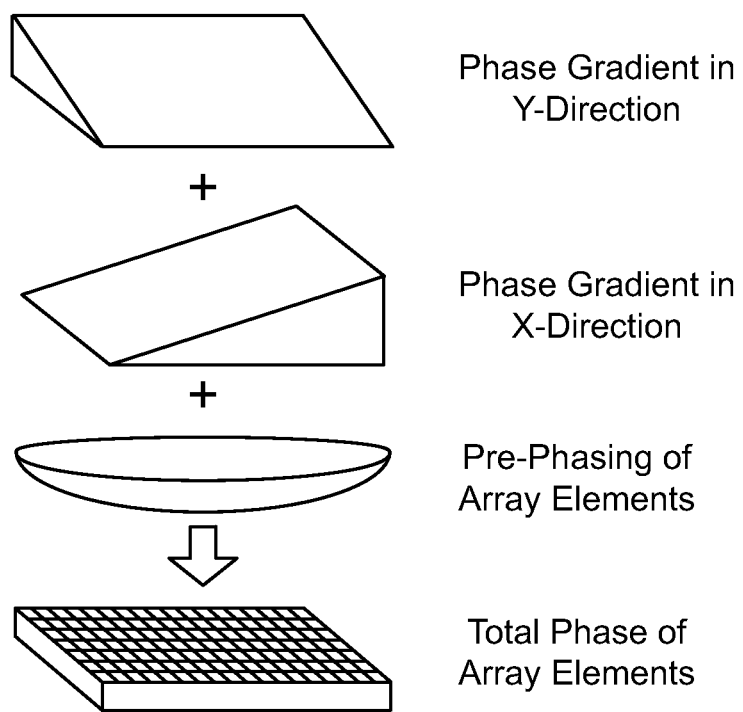
FIG. 4 shows the phases resolved into different components.

FIG. 4 describes how the required phases can be broken down into three separate components. The first two are phase gradients in the x and y direction. These are linear functions of the x and y location of the array elements and hence are relatively inexpensive to compute.

If the receiver-stimulator is very far away from the controller-transmitter only these first two components of the phase are required. However, if the receiver-stimulator is around the border region of the far-field of the array and certainly if it is within the near field, a third component shown as the pre-phasing component is required. This pre-phasing component is not a linear function of the position of the transmit element within the array and is therefore more expensive to compute.

The basic scheme is to calculate the pre-phasing component infrequently and to compute the linear component of the phases whenever the array needs to be steered to a new location. Several options exist for determining the pre-phasing component. One is to calculate the pre-phasing as the phase required to steer to a centered target (directly perpendicular, no off angle-steering) at a nominal expected range (distance) between the controller-transmitter and the receiver-stimulator. This can be done using the equation (Equation 1) shown above. The pre-phasing compensates for the fact that the receiver-stimulator is not strictly in the far-field, which is only true if it is infinitely far away from the controller-transmitter. If it were in the far-field the pre-phasing component would simply be zero, i.e., all elements in the array transmitting with the same phase. These pre-phases can be calculated and stored in read-only memory (ROM) and downloaded as part of the manufacturing of the controller-transmitter or alternatively determined once when the controller-transmitter is implanted. The latter scheme has the advantage of more exact knowledge of the range between the controller-transmitter and receiver-stimulator.

The linear phase gradients can be computed by the control circuitry and then downloaded to each of the phase controllers $241ij$ or the phase controllers can determine the linear phase components using either a look up table or dedicated computation circuitry.

Another alternative is to calculate the pre-phasing based on the nominal location of the receiver-stimulator (i.e., not just the range but also the angular location). This works well if the receiver-stimulator is located at a significant angle from perpendicular to the controller-transmitter. If there is not significant movement of the receive-stimulator relative to the controller-transmitter, the pre-phasing component only needs to be computed once saving significant computational overhead.

The electrical output produced through electrodes 155 as part of the scanning process may be considered a stimulation or pacing output, if sufficient energy is contained in the output to excite the tissue adjacent to electrodes 155; however, it is not required that the tissue be stimulated to detect the electrical signal at electrodes 145. In fact, it is advantageous for the electrical output to not be a stimulating pulse because the energy required to produce an electrical output that is detectable by electrodes 145 and detection circuits 241 is significantly lower than the energy required to stimulate tissue. This lower energy requirement is primarily achieved by shortening the duration of the locator signal and resulting electrical output at electrodes 155 to a value that is significantly below that used to stimulate tissue. For example, signal durations for cardiac tissue stimulation are in the range of 200 µs to 2000 µs, while typical durations are in the 400 µs to 500 µs range. The minimal duration of a locator signal is affected by various parameters: the operating frequency of the system, the Q of both transmitter and receiver transducers as well as the size of the transmit array and overall receiver structure if it contains multiple transducers. A minimal time of 10 cycles is a reasonable estimate. For an ultrasound system operating in the 500 kHz to 1 MHz frequency range this sets the minimum locator signal duration at 10 to 20 µs—at least 20 times shorter than the typical duration for tissue stimulation. This results in at least 20 times less energy used for transmitting the locator signal than that used to stimulate the tissue, making this embodiment attractive.

Short duration locator signals require different detection circuits 241 than that used for conventional ECG processing or even pacing spike detection. ECG signals are typically processed with an amplifier bandwidth of 0.5 Hz to 100 Hz. Pacing spike detectors typically have a bandwidth of 1 kHz to 2.5 kHz. A 10-20 µs electrical signal produced in response to 10-20 µs locator signal requires a bandwidth of up to 100 kHz.

Research on both animal models and humans indicate that it is common to observe signal attenuation of 65-80 dB for a pacing signal generated from within the heart and sensed on surface ECG electrodes. Therefore a 1 volt electrical pulse delivered across electrodes 155 would result in a 560 microvolt to 100 microvolt signal on electrodes 145. State of the art amplifiers can achieve noise figures in the range of 20 nV/(Hertz)$^{1/2}$, resulting in noise on the order of 6 microvolts over a 100 kHz bandwidth, resulting in a very reasonable signal to noise ratio for detection of a location signal. However, such high bandwidth, high gain amplifiers consume more power than conventional ECG amplifiers which are amplifying lower bandwidth higher amplitude signals. It is therefore advantageous to only turn on these amplifiers when they are required, i.e., immediately following transmission of acoustic locator signals.

Figure 5A:
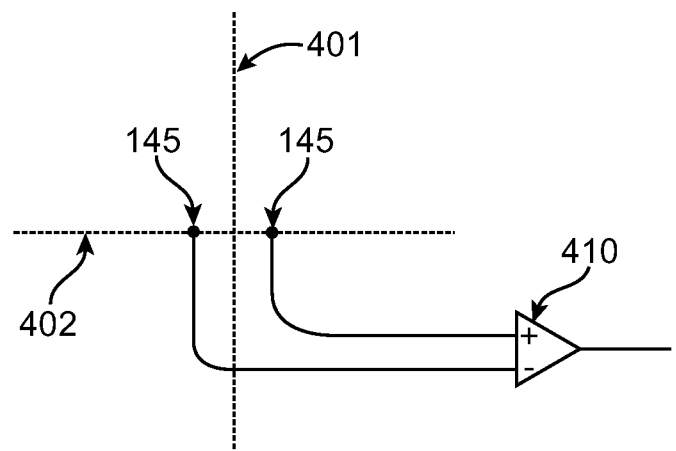
FIGS. 5A-5C show various electrode configurations.
Figure 5B:
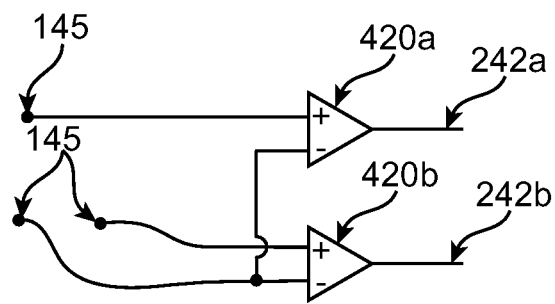
Figure 5C:
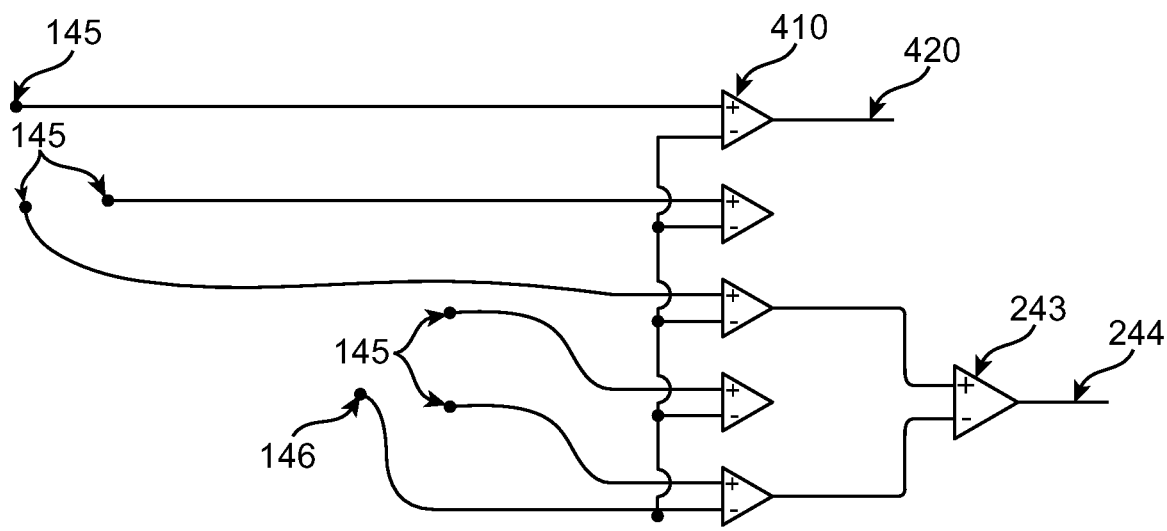

Additionally it is important to note that the location signal is generated and sensed from two electrodes that are spatially close to each other. The positions of both, receiver-stimulator electrodes 155 and controller-transmitter electrodes 145, are constrained by practical limitations. Hence, the electrical signal produced by electrodes 155 will have a dipole radiation pattern and the sensitivity of the electrodes 145 will have a dipole pattern as well. FIG. 5a shows a typical dipole arrangement. Sensing electrodes 145 are input into a differential amplifier 410. The dashed line 401 indicates a region, a "blind spot", where a signal source cannot be sensed by the electrodes 145. This is because a signal source placed along this line is equidistant to both electrodes 145 and the differential amplifier subtracts these two equal signals producing a null output. Correspondingly, the dashed line 402 indicates a region where a signal source will be sensed with maximum output from the amplifier 410. A similar behavior occurs as a result of the transmission of the electrical signal through electrodes 155. Therefore, the overall attenuation will be the result of the superposition of two dipole patterns. In order to avoid potential "blind spots" in these dipole patterns it is, therefore, advantageous to use more than two electrodes 145 on the controller-transmitter. FIG. 5b shows how the addition of a third electrode eliminates the problem of this "blind spot". Two amplifiers 420a and 420b are used to amplify signals from two separate dipoles oriented 90 degrees apart. The two signal outputs, 242a and 242b of 420a and 420b, respectively, are then analyzed for the presence of the location signal. Even more improvements can be made by the addition of more electrodes that are spatially separated from the first three electrodes as shown in FIG. 5c. This has the additional benefit of avoiding any "blind spots" in the dipole pattern generated by electrodes 155 at the receiver-stimulator. One electrode 146 is chosen as a reference and all other electrodes 145 are amplified relative to this reference using amplifiers 410i each of which produces a signal 420i. The dipole signal 244 from any pair of electrodes can then be calculated by taking the difference between two of the output signals 420i, using 243 which can be implemented either as a hardware differential amplifier or in software as the subtraction of two digitized signals. As discussed above, the amplifiers 410i are necessarily high bandwidth, high gain amplifiers and therefore consume significant power. Therefore, it is advantageous to only use those that provide the largest amplitude location signals. Assuming that the motion of the receiver-stimulator and controller-transmitter will significantly change the amplitude of the location signal, once the electrode pair that produces the largest location signal is determined, only the amplifiers used to produce this signal need to be used, significantly reducing power consumption.

An important consideration is the time taken to determine the location of the receiver-stimulator. Obviously, this time should be as short as possible. If this time is comparable to the cardiac cycle, then motion of the heart between determination of the location and subsequent delivery of stimulation energy becomes problematic. It is also advantageous to minimize the required scan time when the leadless stimulator is used concomitantly with a standard pacemaker to achieve therapeutic bi-ventricular pacing. In this case, as disclosed in pending application Ser. No. 11/315,023, the controller-transmitter transmits acoustic energy to stimulate the heart immediately following the detection of a right ventricular (RV) pacing artifact in the concomitantly implanted device. Preferably, the determination of the receiver-stimulator position is done after the detection of the RV pacing artifact so that the effect of cardiac motion between position determination and stimulation is minimized.

FIG. 6 shows several methods for minimizing the required scan time. FIG. 6a shows a partition of the space to be scanned into different target regions. The partition assumes there is no depth targeting and therefore the scan space is in the x-y plane at a fixed z location. The method can be easily extended to the case of depth targeting. The speed of sound in the soft tissue and blood is approximately 1.5 mm/μsec. Considering a large distance between the controller-transmitter and receiver-stimulator of 200 mm results in a maximum time of flight of approximately 133 μsec. FIG. 6b shows a simple scan method where the time between locator signals, P, is chosen to be greater than the expected time of flight. A method for processing the output signal 244 is described as follows. Detection of the location signal 510, following a locator signal 505, indicates that the receiver-stimulator is contained in the volume corresponding to the locator signal 505 (volume 15 in FIG. 6a). Furthermore, the time of flight which is proportional to the range between the controller-transmitter and the receiver-stimulator can be measured by the time delay between transmission of the locator signal and detection of the location signal.

FIG. 6c demonstrates a faster scanning method. In this case, the time between transmit pulses (locator signals), P, is shorter than the actual time of flight and is limited only by the duration of each individual locator signal and the setup time for the controller-transmitter to prepare for the next locator signal. This results in multiple locator signals in flight simultaneously between the controller-transmitter and receiver-stimulator, considerably reducing the scanning time. Once a location signal is detected, determination of the actual locator signal that produced the location signal requires knowledge of the nominal time of flight between the controller-transmitter and receiver-stimulator as shown in FIG. 6c. This optimized scheme is applicable if the previous location and hence time of flight to the receiver-stimulator is known and only small movements of the receiver-stimulator relative to the controller-transmitter are expected. The time between locator signals, P, can be set to the maximum expected range of motion. For example, if the maximum possible motion is 40 mm then P must be at least 40/1.5 or 27 μsec.

During initial operation, when the location of the receiver-stimulator and hence nominal time of flight is totally unknown, a hybrid technique as shown in FIG. 6d can be used. A rapid scan of the entire region is performed using a technique similar to that shown in FIG. 6c until a location signal is detected. Once a location signal is detected a slower scan similar to that shown in FIG. 6b is performed for the volumes near the detected location signal (starting with volume 13 then 14, etc.) This will pinpoint the exact volume (in this case 15) and allow back calculation of the actual time of flight.

In some cases, a longer duration between locator signals than that used in FIG. 6b may be required. This can happen if there is sufficient acoustic energy from the locator signal is reflected off anatomical structures in the body and the receiver-stimulator responds to these reflected locator signals. Generally, this is handled by increasing the time between locator signals such that any reverberation or reflection from a previous locator signal has decayed before transmitting another locator signal. However, the likelihood of this problem occurring can be substantially reduced by prior knowledge of the nominal time of flight. This allows the controller-transmitter to look for a location signal over a narrow time window eliminating false detections due to reflected locator signals.

Another strategy for minimizing the scan time and the energy expended on the scan itself is to perform an intelligent search. One approach is to start the scan by transmitting a locator signal to the previous known position of the receiver-stimulator. Therefore, if the receiver-stimulator has not moved outside of the scan volume, only one locator signal is required. If more scanning is required, another strategy is to expand the search out from the last known position for the receiver-stimulator. Another approach is to remember the previous history of motion of the receiver-stimulator and use this to intelligently scan for it. This will greatly reduce the number of scans whenever the primary motion of the receiver-stimulator is periodic for example due primarily to cardiac and respiratory motion.

It should be noted that more than one receiver-stimulator could be implanted and operated using the different approaches described above for optimizing energy transmission. The location of each receiver-stimulator relative to other receiver-stimulators can be registered during the time of implantation. Following implantation, when the receiver-stimulators move due to cardiac motion, breathing, etc., they are likely to move in concert with each other. However, the relative location of the receiver-stimulators with respect to the controller-transmitter, which impacts the optimal energy transmission by the controller-transmitter, is likely to change due to cardiac motion, breathing, etc. To address this issue, if the location of the first receiver-stimulator is identified using one of the approaches described above, the location of the other receiver-stimulators is immediately computed, based on the relative location of the other receiver-stimulators that was registered during implantation.

Alternatively, each receiver-stimulator (when multiple receiver-stimulators are implanted) can be "addressed" using a locator signal with a unique frequency or phase. The approaches described earlier can then be used sequentially for each receiver-stimulator to optimize the energy transmission from the controller-transmitter. Or more simply, if multiple receiver-stimulators are implanted with sufficient difference in location, each could be located directly by the previously described methods, based on knowledge of previous location and the fact that relative locations between devices are unlikely to change significantly.

While the location signal has been detailed as an electrical signal it should be understood that the location signal may be of any nature that can be detected by a controller-transmitter. For example it could be a passive echo from the device or the receiver could be adapted to transmit an acoustic signal in response to the locator signal.

Figure 7A:
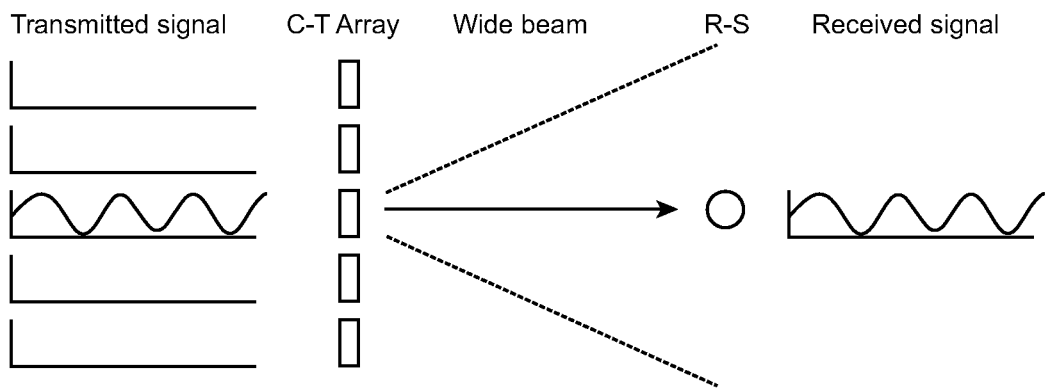
FIGS. 7A-7C illustrate an embodiment using frequency shifting for acoustic beam steering and optimizing energy transmission.
Figure 7B:
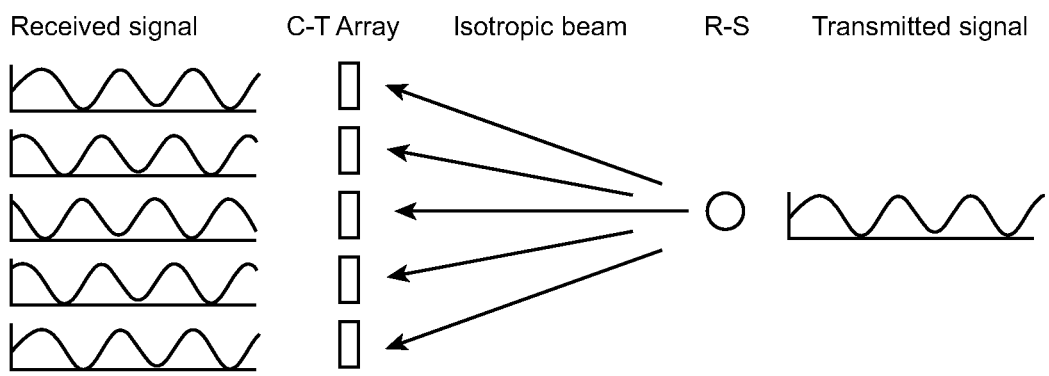
Figure 7C:
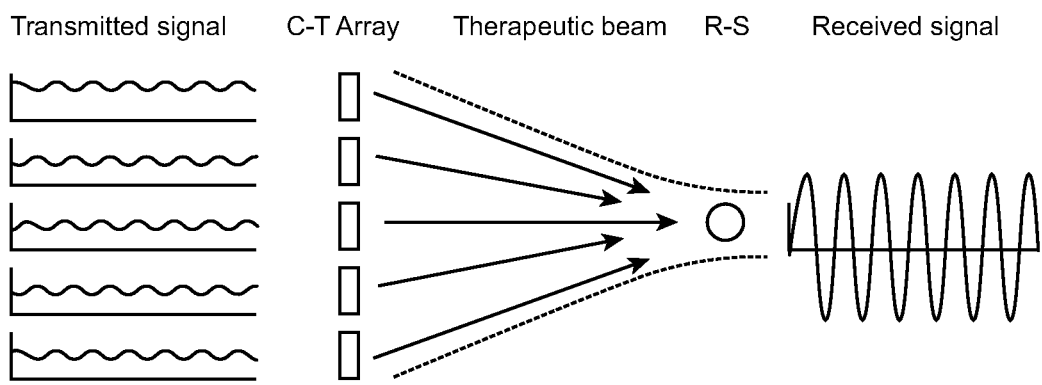

Another embodiment of the invention described here for optimizing energy transmission from a controller-transmitter is illustrated in FIGS. 7A-7C. In FIG. 7A, one element of the controller-transmitter array ("C-T Array") transmits a wide beam acoustic burst (locator signal), which is received by the receiver-stimulator ("R-S"). As the signal is being received in the receiver-stimulator, it is frequency shifted and retransmitted isotropically back to the controller-transmitter, as depicted in FIG. 7B. This retransmission occurs as the locator signal is being received by the receiver-stimulator. The location of the receiver-stimulator with respect to each element of the C-T array is recorded into the memory of the controller-transmitter as the detected phase received per channel. Then, at the clinically appropriate time, the controller-transmitter uses the recorded phase measurements to transmit acoustic energy as a focused beam to the receiver-stimulator to be delivered to electrodes for stimulation of tissue, as shown in FIG. 7C.

The amount of energy contained in the locator signal generated from a single element in the phase measurement mode described above may be substantially greater than that used for stimulation. However, because the correct phase measurements have been obtained, significantly less energy will be transmitted for the stimulation by the entire array than would have been required to achieve the same level of energy delivered to the tissue using a wide beam. Now each element of the array would transmit a focused beam that is much more efficient, compared to the wide beam each element would have transmitted in the absence of the correct phase measurement. Additionally, in the method described above, phase measurements were obtained without additional computations, thus further minimizing the energy consumption.

Upon creation of the focused beam used for stimulation, not all elements of the array need necessarily be driven at the same amplitude. If one pathway or the other from the receiver-stimulator to the array of elements shows either more or less attenuation, this may be overcome by transmitting with either more or less energy, respectively, or by completely turning off severely impacted array elements. Further, it is well known in the art of array design, that aperture shading (lower amplitude emissions from the edges of the array) has the effect of flattening the acoustic beam, for a greater uniformity within the beam. This can also be accomplished, guided by pre-programmed computations in the controller-transmitter.

Additional aspects of the invention are described below. In one embodiment where no locator signal is required, the receiver-stimulator first receives acoustic energy from the controller-transmitter, stores part of the received energy and directs the rest to the tissue. The stored energy could be anywhere from 0 to 100%, and ideally about 5%, of the received energy. Based on a variable, fixed or periodic timeout within the receiver-stimulator, but before the next transmission of acoustic energy from the controller-transmitter, the stored energy is used by the receiver-stimulator to generate a location signal. The location signal may be an electrical signal, or it may be an acoustic transponder signal transmitted to the controller-transmitter, or a similar signal generated by the receiver-stimulator as a homing beacon to signal the location of the receiver-stimulator. The controller-transmitter receives the location signal and computes the location of the receiver-stimulator, using information, such as amplitude, phase, arrival time, or the like from the location signal. Having identified the location of the receiver-stimulator, the controller-transmitter is then able to focus the transmitted acoustic beam to the location or region of the receiver-stimulator and thereby transmit energy or exchange communication optimally.

Alternatively, the controller-transmitter transmits a locator signal in the form of sufficient acoustic energy to a passive receiver-stimulator that uses all the energy received to generate a location signal. In this embodiment the receiver-stimulator would be adapted to have a state machine that switches between using acoustic energy for location signals and using acoustic energy for functional purposes such as stimulation. The location signal is received by the controller-transmitter, which determines the location of the receiver-stimulator based on signal characteristics contained in the location signal and then generates a focused beam that is targeted at the location or region of the receiver-stimulator.

As indicated above, it should be noted that the acoustic receiver of the present invention can function as a receiver-stimulator or a receiver-converter, where the receiver-converter can act as a diagnostic tool. While the examples illustrate the receiver-stimulator embodiments, the energy optimization techniques described above are equally applicable for a receiver-converter.

While the above is a complete description of the preferred embodiments of the invention, various alternatives, modifications, and equivalents may be used. Therefore, the above description should not be taken as limiting the scope of the invention, which is defined by the appended claims.

What is claimed is:

1. A system for acoustic energy into a human body comprising:
   an array of acoustic transducers configured to transmit acoustic energy into the body;
   circuitry for focusing the acoustic energy at specific regions in the body;
   an acoustic receiver adapted to receive the focused acoustic energy and convert the acoustic energy into electrical energy;
   a pair of electrodes connected to the acoustic receiver and adapted to transfer the electrical energy through the body;
   wherein the circuitry is further configured to detect the electrical energy transferred through the body by the pair of electrodes to determine whether the acoustic energy is focused on the acoustic receiver.

2. The system of claim 1, wherein the circuitry further comprises one or more pairs of electrodes that are configured to determine whether the acoustic energy is focused on the acoustic receiver.

3. The system of claim 2, wherein the circuitry is further configured for sequentially transmitting the acoustic energy.

4. The system of claim 1, further comprising a controller-transmitter and a receiver-stimulator, wherein the controller-transmitter comprises the transducer array and the circuitry and the receiver-stimulator comprises the acoustic receiver and is adapted to be implanted in the body.

5. The system of claim 4, wherein the controller-transmitter is configured to transmit an acoustic locator signal into the body and the receiver-stimulator is configured to generate a location signal in response to receiving the locator signal, wherein the location signal is used by the controller-transmitter to direct a focused acoustic beam towards the receiver-stimulator.

6. The system of claim 5, wherein the controller-transmitter is further configured to detect the location signal and the transducer array is configured to sequentially steer an acoustic beam to transmit the locator signal to regions in the body until the location signal is detected or a preset time limit has been reached.

7. The system of claim 6, wherein the transducer array and the circuitry are configured to transmit the locator signal as a focused acoustic beam.

8. The system of claim 7, wherein the controller-transmitter is further configured to adjust the transducer array to transmit focused acoustic energy to the region of the body associated with detecting the location signal.

9. The system of claim 8, wherein the electrical energy converted from the focused acoustic energy by the receiver-stimulator and transferred to the body is sufficient to stimulate tissue.

10. The system of claim 9, wherein the tissue is cardiac tissue.

11. The system of claim 10, wherein the location signal is an electrical energy output applied to the pair of electrodes.

12. The system of claim 11, further comprising a sensing circuit and one or more sensing electrodes adapted to be in electrical communication with the body, wherein the location signal is detected by the sensing circuit.

13. The system of claim 12, wherein the circuitry further comprises the sensing circuit and the sensing electrodes.

14. The system of claim 13, wherein the controller-transmitter is adapted to be implanted in the body.

15. The system of claim 14, wherein the sensing circuit comprises a spike detector assembly.

16. The system of claim 15, wherein the controller-transmitter is configured to (1) determine whether the focused acoustic beam is targeting the receiver-stimulator by characterizing the location signal that is detected by the spike detector assembly using one or more signal characteristics; and (2) adjust the focused acoustic beam to target another region of the body where the receiver-stimulator may be located.

17. The system of claim 16, wherein the controller-transmitter is further configured to determine that the focused acoustic beam is targeting the receiver-stimulator when the characterizing indicates that the location signal is detected within at predetermined time frame.

18. The system of claim 17, wherein the transducer array is further sequentially adjusted to transmit focused acoustic beams as a sequence of locator signals towards a sequence of regions of the body, and wherein characterizing the location signal following any one of the locator signal transmissions indicates whether the focused acoustic beam is targeting the region of the body implanted with the receiver-stimulator.

19. The system of claim 17, wherein the electrical energy output is less than the amount required to stimulate tissue and wherein the tissue is cardiac tissue.

20. The system of claim 17, wherein the electrical energy output is sufficient to stimulate tissue and wherein the tissue is cardiac tissue.

21. The system of claim 12, wherein the sensing circuit and the sensing electrodes are located on a device with the sensing electrodes configured to be in electrical communication with the external surface of the body.

22. The system of claim 12, wherein the sensing circuit is a spike detector circuit.

23. The system of claim 12, wherein the detected location signal indicates whether the transducer array is focused on the region of the body implanted with the receiver-stimulator.

24. The system of claim 6, wherein the controller-transmitter is further configured to adjust the transducer array to transmit focused acoustic energy to the region of the body associated with detecting the location signal.

25. The system of claim 24, wherein the electrical energy converted from the focused acoustic energy by the receiver-stimulator and transferred to the body is sufficient to stimulate tissue.

26. The system of claim 25, wherein the tissue is cardiac tissue.

27. The system of claim 4, wherein the receiver-stimulator is configured to periodically generate a location signal, and wherein the controller-transmitter is configured to detect the location signal, wherein the location signal is used by the controller-transmitter to direct a focused acoustic beam towards the receiver-stimulator.

28. The system of claim 27, wherein the location signal is an electrical energy output, wherein the electrical energy output is detected by a sensing circuit which uses one or more sensing electrodes adapted to be in electrical communication with the body.

29. The system of claim 27, wherein the receiver-stimulator is adapted to generate an acoustic output and the location signal is an acoustic transmission.

30. The system of claim 27, wherein the transducer array is adjusted using electrical drive signals to transmit focused acoustic energy towards the receiver-stimulator based on the characteristics of the location signal that is detected by the controller-transmitter.

31. The system of claim 30, wherein the electrical energy converted from the focused acoustic energy by the receiver-stimulator and transferred to the body is sufficient to stimulate tissue.

32. The system of claim 30, wherein the electrical drive signals to the transducer array are adjusted based on one or more parameters including frequency, duration, amplitude, phase, and time of flight of the location signal.

* * * * *

UNITED STATES PATENT AND TRADEMARK OFFICE
CERTIFICATE OF CORRECTION

PATENT NO. : 8,718,773 B2
APPLICATION NO. : 11/752775
DATED : May 6, 2014
INVENTOR(S) : N. Parker Willis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1134 days.

Signed and Sealed this
Tenth Day of May, 2016

Michelle K. Lee
*Director of the United States Patent and Trademark Office*